United States Patent [19]
Cockrum

[11] Patent Number: 5,645,834
[45] Date of Patent: Jul. 8, 1997

[54] METHOD AND PRODUCT FOR TREATING FAILURE OF PASSIVE TRANSFER AND IMPROVING MILK PRODUCTION IN BOVINE SPECIES

[75] Inventor: Richard H. Cockrum, Minburn, Iowa

[73] Assignee: Immuno-Dynamics, Inc., Perry, Iowa

[21] Appl. No.: 239,886

[22] Filed: May 9, 1994

Related U.S. Application Data

[63] Continuation-in-part of Ser. No. 937,540, Aug. 28, 1992, abandoned.

[51] Int. Cl.$^6$ .................. A61K 39/395; A61K 38/02; A61K 38/30; A61K 38/40
[52] U.S. Cl. .................. 424/130.1; 514/2; 514/21; 530/387.1; 530/414; 530/832; 530/833
[58] Field of Search ................ 530/387.1, 414, 530/832, 833; 424/130.1; 514/2, 21

[56] References Cited

U.S. PATENT DOCUMENTS

| | | | |
|---|---|---|---|
| 4,051,235 | 9/1977 | Plymate | 424/85 |
| 4,644,056 | 2/1987 | Kothe et al. | 424/85 |
| 4,816,252 | 3/1989 | Stott et al. | 424/85.8 |
| 4,834,974 | 5/1989 | Stott et al. | 424/85.8 |
| 5,151,449 | 9/1992 | Milgram | 514/654 |

FOREIGN PATENT DOCUMENTS

| | | |
|---|---|---|
| 0391416A1 | 10/1990 | European Pat. Off. . |
| 040275300A | 9/1992 | Japan . |
| 9202538 | 2/1992 | WIPO . |

OTHER PUBLICATIONS

Satija, K.C. et al, Infect & Immun, 24(2):567–70, May 1979.
Yokoharma, M et al, Jpn. J. Zootech Sci, 60(5):450–458, 1989 (Abst Only).
Welsh, JK et al, J. Pediat, 94(1):1–9, 1979.
Mellor, D.J. et al, Q.J. Exp. Physiol, 72(3):345–356,1987.
Barta, O. 91 "Inhibition of Lymphocyte Blastogenesis by Whey", *American Journal of Veterinary Research* 52(2):247–253.
"Immunity in the Mammary Gland", *Immunological Surface—Protective Mechanisms*, 161–164.
McGuire, T. 1982. "Failure of Colostral Immunoglobulin Transfer to Calves: Prevalence and Diagnosis:, The Compendium on Continuing Education" 4(1): Article #10 S35–S37.

Besser, T.E. 1990. "Decreased Colostral Immunoglobulin Absorption in Calves With Postnatal Respiratory Acidosis", *Journal of American Veterinary Medical Association* 196(8):1239–1243.
Besser, T.E., 1988. "Passive Immunity to Bovine Rotavirus Infection Associated with Transfer of Serum Antibody Into The Intestinal Lumen", *Journal of Virology* 2238–2242.
Liu, I.K.M. 1991. "Evaluation of Intravenous Administration of Concentrated Immunoglobulin G to Colostrum-Deprived Foals". *American Journal of Veterinary Research* 52(5):709–712.
Klobasa, F. 1990. "Maternal–Neonatal Immunoregulation: Suppression of De Novo Synthesis of IgG and IgA, But Not IgM, in Neonatal Pigs by Bovine Colostrum, Is Lost Upon Storage:". *American Journal of Veterinary Research* 51(9):1407–1412.
Tizard, I. 1982. "Regulation of the Immune Responses", *An Introduction to Veterinary Immunology* 2nd Ed. 93–104 (Chapter 7).
Tizard, I. 1982. "Immunity in the Fetus and Newborn Animal", *An Introduction to Veterinary Immunology*, 2nd Ed. Chapter 11, 165–177.
Smith, K.L. 1981. "Lactoferrin: A Component of Nonspecific Defense of the Involuting Bovine Mammary Gland" In; J.E. Butler (ed.) *The Ruminant Immune System. Advances in Experimental Medicine and Biology* 137:535–554.
Kehrli, "In Vivo Effects of a Thymosin$\alpha_1$–Containing Colostral Whey Product on Neutrophils and Lymphocytes from Lactating Cows Without and With Experimentally Induced Staphylococcus aureus Mastitis", *Veterinary Immunology and Immunopathology*, 20 (1989) 149–163, Elsevier Science Publishers B.V., Amsterdam—Printed in The Netherlands.

*Primary Examiner*—Susan A. Loring
*Attorney, Agent, or Firm*—Zarley, McKee, Thomte, Voorhees, & Sease

[57] ABSTRACT

A product and method of treating failure of passive immunity transfer and for stimulating growth and milk production in cows by administration of proteins purified from bovine colostrum is disclosed. Injecting, either subcutaneously or intravenously, prepared bovine colostrum containing immunoglobulins and nonspecific proteins increases immunoglobulins in the blood stream to effect passive transfer after gut closure. Also administration in spray dried form as a diet supplement to growing calves or adult cows improves growth and milk production due to the presence of previously unappreciated nonspecific proteins.

18 Claims, 1 Drawing Sheet

METHOD AND PRODUCT FOR TREATING FAILURE OF PASSIVE TRANSFER AND IMPROVING MILK PRODUCTION IN BOVINE SPECIES

CROSS-REFERENCE TO A RELATED APPLICATION

This application is a continuation in part of patent application Ser. No. 07/937,540 filed Aug. 28, 1992, now abandoned, the disclosure of which is incorporated by reference.

BACKGROUND OF THE INVENTION

Bovine colostrum is a unique secretion of the mammary gland which is produced during the first few days of lactation. This secretion differs a great deal from normal milk. All of its components are not known, however it has been recognized to be very rich in immunoglobulins for the newborn. Intake of colostrum is essential during the first 24 hours of a calf's life. Due to the structure of the bovine placenta, transplacental transfer of immunoglobulins which confers passive immunity in most mammals is negligible. In this species nearly all passive transfer occurs by way of colostrum which is absorbed by the calf. The immunological components of colostrum include specific immunoglobulins IgG, IgM, IgA which convey passive immunity to the newborn. Peak serum immunoglobulin levels in colostrum are normally reached between 12 and 24 hours after birth. The calves intestinal permeability to these proteins is generally highest immediately after birth and declines after about six hours.

After this "window of opportunity" there is gut closure and further immunoglobulin absorption through the gut becomes negligible. Consequently calves over twenty-four hours old are essentially incapable of absorbing necessary immunoglobulins for passive transfer of immunity. This difficulty is termed failure of passive transfer (FPT) and is characterized by insufficient numbers of immunoglobulins present in the bloodstream prior to gut closure.

This failure prevents the protection of the newborn from most pathogens encountered until the animal's own immune system is exposed to various disease antigens and produces its own immunoglobulins to these diseases.

While the role of colostrum in conferring passive immunity during the critical first hours of a neonate's life has long been appreciated, virtually no recognition to date has been made of colostrum's potential benefits after gut closure.

Consequently, methods of assisting the health of calves over 24 hours old or even adults have concentrated on purified traditional milk and conventional thinking has been the colostrum would serve no useful purpose after gut closure. As a result purified traditional milk and other methods such as administration of the highly controversial bovine growth hormone have been explored. While bovine growth hormone, when administered, has been shown to increase milk production, milk quality has suffered. There is also a psychological problem in that many consumers refuse milk from so treated dairy cows.

Still other methods have included use of genetic markers to improve overall health and performance of cows. Thus a particular genotype may be screened for aid in selection of dairy cows which possess underlying genetic criteria which will result in a desirable phenotype.

Despite all of these developments, many expensive and involving controversial technology, no one to date has recognized the potential use of all-natural colostrum for improvement of calf and adult cow health and performance by consistent and regular dosing after gut closure.

While the presence and necessity of specific immunoglobulins in colostrum has long been appreciated, little or no attention to date has been paid to the plethora of additional non specific proteins found in colostrum. Current research has shown that colostrum contains several nonspecific proteins, for example transferin and lactoferin which bind iron, an essential growth factor for most aerobic bacteria. Enzymes such as lysozyme, xanthine oxidase and lactoperoxidase, which have been shown to have antimicrobial activity, particularly in the gut are present. Insulin-like growth promoting factors which increase uptake of glucose and amino acids by cells in the body, are present. Further, colostrum contains several additional components like conglutinin and the basic proteins β-lysin and ubiquitin, although scientific knowledge of the function of those is limited. These important characteristics of colostrum, it has now been discovered, can be used in treatments after gut closure.

Thus it is an object of the present invention to make use of colostrum as an aid to improve overall health and performance of calves and cows, particularly after gut closure.

It is yet another object of the present invention to prepare a purified injectable product derived from colostrum which includes these proteins and is useful after infancy, recognizing the continuing benefits of these proteins in even adult cows.

Further there exists a great need for a method of treating failure of passive immunity after gut closure and an object of the invention is to provide a treatment of FPT by injection of purified colostrum immunoglobulins and nonspecific proteins directly into the calf, with a high efficacy.

Another object of the invention is to provide a method of improving weight gain by calves by use of a dietary supplement of proteins derived from colostrum.

Yet another objective is to increase daily milk production in adult cows by use of a dietary supplement of proteins derived from colostrum. The method of accomplishing these and other objectives will become apparent from the following description of the invention.

SUMMARY OF THE INVENTION

The invention relates to use of colostrum to prepare a protein rich whey product which has a number of uses. The invention relates to a method of stimulating growth in calves by addition of a dietary supplement of dried colostrum derived proteins in particular amounts. It relates to a method of stimulating milk production in dairy cows by again administering the product as a dried diet supplement. Further the invention contemplates uses of the protein rich product as a treatment of FPT, by parental administration of the product in a sterile injectable liquid form, again in specified amounts. These uses are all based on the discovery and appreciation of the protein components of colostrum both nonspecific and immunologically active.

DETAILED DESCRIPTION OF THE INVENTION

Figure 1:
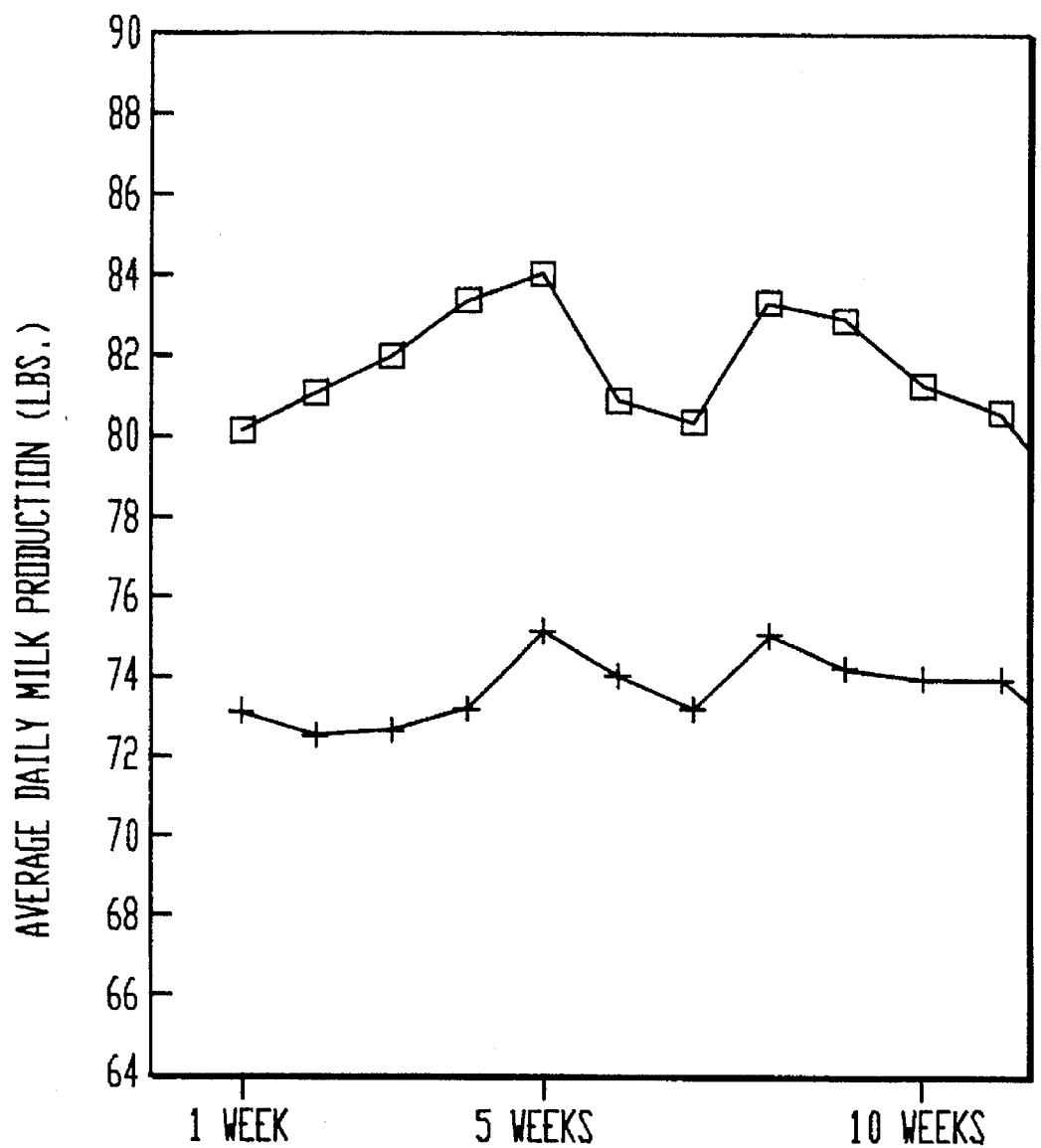
FIG. 1 is a graph demonstrating the increase in average daily milk production for cows treated with the method of the invention. A square indicates a supplemented diet while a + indicates a normal diet.

As previously stated the invention comprises several uses of a purified protein product derived from colostrum. One method of collecting and purifying the bovine colostrum to concentrate levels of specific antibodies resulting from exposure to selected antigens is disclosed in Plymate, U.S. Pat. No. 4,051,235. Contrary to methods such as this, the product of this invention concentrates not just IgG but all other proteins present in colostrum. Traditional thinking as exemplified by Plymate is that it is the immunoglobulins alone which are important in colostrum.

This invention acknowledges that colostrum can be valuable in parentally imparting passive immunity after gut closure but also is quite valuable for its other components. Calves treated with the colostrum derived protein whey as a dried diet supplement experienced increased weight gain over those without supplement. Also, those adults receiving the supplement had increased daily milk production compared to control and finally when administered in injectable liquid form the product increases serum immunoglobulin levels. As used herein, the term whey shall mean a purified colostrum derived product from which fat and casein have been removed comprising immunoglobulins and other proteins as earlier described, and is specifically intended to exclude whey derived from other sources such as noncolostrum-type milk.

PREPARATION OF COLOSTRUM

First milking colostrum is procured from Grade A dairy herds located throughout different areas. Once collected, colostrum filled containers are frozen until needed. Upon production demand colostrum is thawed at ambient temperature for 8 to 24 hours and emptied into a vessel.

Casein and fat are removed from the colostrum mixture by introduction of one-half of an ounce of calcium chloride and one ounce of microbial rennet per ten gallons of colostrum.

The colostrum is agitated and the temperature is elevated to 85° F. by hot water heat exchangers. Coagulation begins and the agitators are shut off. The resulting curd is cut with curd knives to allow fat to float into and through the curd. The fat is then trapped within, and on top of, the curd, resulting in a nearly fat-free whey.

The colostrum derived whey is filtered to remove microorganisms and finally passed through a cream separator to remove any remaining fat. The treated and preserved whey is then stored in a refrigerated tank at 2° C. to 5° C. The whey is then filtered and reduced in volume. The resulting concentrated product is then adjusted to a pH of 6.4 to 6.6 by the addition of 2% sodium hydroxide or any other acceptable method. The protein content is diluted to 6–7% by the addition of physiological saline solution. The whey is then filter sterilized for administration to calves. The resulting whey, which contains immunoglobulins and nonspecific proteins, is safely injectable, and its effectiveness is not dependent on oral administration and absorption across the gut during the relatively short "window of opportunity".

The whey is eventually placed in 120 ml serum bottles and stored in a cooler at 37° F. plus or minus 3° F. Afflicted calves are then treated with the sterile whey product. Calves under 1–21 days old are given the product either orally or subcutaneously in a dosage of 5 ml per pound of body weight. Calves 3 to 7 days of age are given 5 ml per pound of body weight subcutaneously or intravenously. Animals subjected to this treatment experienced an increase in immunoglobulin concentration as illustrated by the following examples. Optionally the product may be spray dried into a powder form for dietary feed supplementation. Further, unexpectedly, when the same product is included in the diet of calves or adult cows in amounts of $\frac{1}{10}$ to $\frac{2}{5}$ oz. per day per animal, the presence of nonspecific and other essential proteins promoted growth, stimulated milk production, and improved the overall health of the animals. It should be noted that amounts are not critical and since the product is all natural virtually any practical amount within the range of economic limits can be administered.

EXAMPLE 1

Effects on Milk Production

A study was conducted in a producing dairy herd at Van Vliet Dairy Farm, Escalon, Calif. over a period of approximately forty (40) weeks. Only first and second calf heifers were included with an average of approximately 440 animals being evaluated on a daily basis for a total of 650 heifers being used in the entire study. Animals in the study had all been properly vaccinated for all appropriate pathogens and in addition producing cows were routinely monitored on a Dairy Herd Improvement (DHI) program for at least two months prior to entering this study and throughout the test period. The cows were all housed in identical fashion and fed the same base rations (standardized Total Mixed Rations(TMR)) throughout the study. Milk production was monitored daily for individual cows. Any cow evidencing a somatic cell count higher than 350,000 was continued on the appropriate regime, but its daily milk production was excluded from the study records. Following standard treatments utilized on the dairy farm and lowering the count below 200,000 the cows daily production was again entered into the study records.

The cows were divided into two major groups, first calf heifers and second calf heifers. Major groups were further divided as follows:

Group A—second calf heifers which received spray dried powdered form of the invention during the first eighteen (18) weeks of the study, were allowed to lapse for two weeks, and remained untreated for the last eighteen (18) weeks of the study.

Group B—second calf heifers which remained untreated during the first eighteen (18) weeks of the study, were allowed to lapse for two weeks, and then received product of the invention for the last eighteen (18) weeks of the study.

Group C—first calf heifers which received product of the invention during the first eighteen (18) weeks of the study, were allowed to lapse for two weeks, and remained untreated for the last eighteen (18) weeks of the study.

Group D—first calf heifers which remained untreated during the first eighteen (18) weeks of the study, were allowed to lapse for two weeks, and then received product of the invention for the last eighteen (18) weeks of the study.

The product of the invention in a dried form was mechanically blended into the bulk standardized Total Mixed Ration on a daily basis. A fixed quantity of ration either with or without the product was fed to each cow daily. During the first 10 days of treatment each animal received a daily dose of 0.4 ounce of the product in its ration. On all subsequent days the dose was equal to 0.2 ounce of the product.

The daily average milk production in each group was calculated based upon the daily output during each week of the study. In all cases, the eighteen (18) week treatment period values were compared with the same group's own values obtained during the eighteen (18) week period when no treatment was given. Upon analysis of the results, it was shown that administration of the product in the diet of first and second calf heifers provided an effective means to increase milk production. There appeared to be no difference in response in terms of increased production in either first or second calf heifers. Overall increase in average daily milk production was 8% during the entire eighteen (18) treatment weeks of the study for all groups evaluated in comparison to the untreated period for the same groups. Secondary analysis of the data indicated that the primary effect of the product in this study occurred during the first 10 weeks after treatment commenced and then slowly diminished. Comparatively the average daily milk production was improved by more than 11% for all groups studied during this period. In contrast a combined change of only 4% was observed during the last eight weeks of treatment period. This differential was seen in both the first and second calf heifers FIG. 1 is a graph demonstrating the increase in average daily milk production for cows treated with the method of the invention.

It is submitted that the unexpected improvement in milk production is a surprising result as colostrum has been characteristically considered only as a source of immunoglobulins. It is clear that there are other proteins in the preparation which have significant effects on overall cow health and productivity. These results could not be simply due to the presence of immunoglobulins in the product as administration occurred after gut closure, indicating the value of the other components in the purified colostrum product.

While not wishing to be bound by any theory, it is submitted that the nonspecific proteins present in the colostrum preparation of the invention contain hormone precursors which may act to stimulate milk production. Applicant is clearly the first to appreciate the benefits of these additional proteins as most supplements are designed to isolate purely immunoglobulins. As in Scott, U.S. Pat. No. 4,834,974 which prepares an immunoglobulin product from liquid by-product from cheese preparation or regular casein removed milk, not colostrum.

Tables 1–4 indicate the specific results obtained on treatment with the method of the invention in the various subgroups.

| | SUMMARY OF EFFECT OF TREATMENT WITH DRIED, PURIFIED COLOSTRUM ON AVERAGE DAILY MILK PRODUCTION (LBS.) IN SECOND CALF HEIFERS | | | | | |
|---|---|---|---|---|---|---|
| | DURING TREATMENT | | | UNTREATED | | |
| Week | No. Days Monitored | Avg. No. Cows | Avg. Daily Production | No. Days Monitored | Avg. No. Cows | Avg. Daily Production |
| | | | GROUP A | | | |
| 1 | 7 | 84 | 87.8 | 6 | 77 | 79.5 |
| 2 | 6 | 84 | 88.5 | 7 | 75 | 79.4 |
| 3 | 7 | 82 | 90.8 | 6 | 74 | 77.6 |
| 4 | 6 | 80 | 91.4 | 7 | 74 | 79.0 |
| 5 | 7 | 81 | 89.2 | 6 | 72 | 80.9 |
| 6 | 7 | 87 | 82.5 | 7 | 70 | 81.1 |
| 7 | 7 | 90 | 82.8 | 5 | 69 | 78.3 |
| 8 | 6 | 90 | 87.9 | 7 | 67 | 78.4 |
| 9 | 7 | 87 | 89.7 | 6 | 67 | 75.0 |
| 10 | 6 | 93 | 87.0 | 7 | 69 | 73.7 |
| 11 | 6 | 96 | 87.2 | 7 | 72 | 74.1 |
| 12 | 6 | 95 | 85.4 | 6 | 74 | 73.5 |
| 13 | 7 | 92 | 85.5 | 6 | 75 | 72.6 |
| 14 | 6 | 89 | 86.0 | 5 | 79 | 74.6 |
| 15 | 7 | 87 | 83.1 | 7 | 76 | 77.2 |
| 16 | 6 | 83 | 83.7 | 4 | 69 | 79.6 |
| 17 | 7 | 82 | 82.8 | 7 | 70 | 80.1 |
| 18 | 7 | 80 | 81.6 | 6 | 71 | 79.8 |
| Mean | 6.6 | 86.8 | 86.3 + | 6.2 | 72.2 | 77.5 |
| Change | — | — | 11.4% | — | — | — |
| Mean (wk. 1–10) | 6.6 | 85.8 | 87.8 + | 6.4 | 71.4 | 78.3 |
| Change | — | — | 12.1% | — | — | — |
| Mean (wk. 11–18) | 6.5 | 88.0 | 84.4 + | 6.0 | 73.3 | 76.4 |
| Change | — | — | 10.5% | — | — | — |
| | | | GROUP B | | | |
| 1 | 6 | 116 | 83.1 | 7 | 79 | 80.0 |
| 2 | 7 | 115 | 84.6 | 6 | 83 | 78.6 |
| 3 | 6 | 118 | 84.0 | 7 | 83 | 80.8 |
| 4 | 7 | 119 | 87.1 | 6 | 87 | 80.0 |
| 5 | 6 | 112 | 91.2 | 7 | 90 | 80.8 |
| 6 | 7 | 112 | 92.0 | 7 | 86 | 79.6 |
| 7 | 5 | 112 | 90.5 | 7 | 85 | 79.2 |
| 8 | 7 | 116 | 92.2 | 6 | 89 | 81.4 |
| 9 | 6 | 116 | 89.5 | 7 | 92 | 82.0 |
| 10 | 7 | 114 | 88.6 | 6 | 93 | 81.9 |
| 11 | 7 | 111 | 88.0 | 6 | 94 | 82.0 |
| 12 | 6 | 110 | 84.2 | 6 | 102 | 80.3 |
| 13 | 6 | 109 | 81.7 | 6 | 106 | 79.8 |
| 14 | 5 | 109 | 82.0 | 7 | 107 | 81.4 |
| 15 | 7 | 107 | 82.7 | 6 | 107 | 81.9 |

-continued

SUMMARY OF EFFECT OF TREATMENT WITH DRIED, PURIFIED COLOSTRUM ON AVERAGE DAILY MILK PRODUCTION (LBS.) IN SECOND CALF HEIFERS

| Week | DURING TREATMENT | | | UNTREATED | | |
|---|---|---|---|---|---|---|
| | No. Days Monitored | Avg. No. Cows | Avg. Daily Production | No. Days Monitored | Avg. No. Cows | Avg. Daily Production |
| 16 | 4 | 106 | 83.5 | 7 | 108 | 81.0 |
| 17 | 7 | 108 | 83.0 | 7 | 115 | 82.1 |
| 18 | 6 | 111 | 81.5 | 7 | 114 | 83.2 |
| Mean Change | 6.2 | 112.3 | 86.1 + 6.4% | 6.6 | 95.6 | 80.9 |
| Mean (wk. 1–10) Change | 6.4 | 115.0 | 88.3 + 9.8% | 6.6 | 86.7 | 80.4 |
| Mean (wk. 11–18) Change | 6.0 | 108.9 | 83.3 + 2.3% | 6.5 | 106.6 | 81.4 |
| GROUP C | | | | | | |
| 1 | 7 | 125 | 77.6 | 6 | 131 | 67.3 |
| 2 | 6 | 123 | 77.5 | 7 | 130 | 66.7 |
| 3 | 7 | 120 | 79.0 | 6 | 129 | 66.2 |
| 4 | 6 | 119 | 78.6 | 7 | 131 | 67.9 |
| 5 | 7 | 118 | 77.7 | 6 | 125 | 70.6 |
| 6 | 7 | 118 | 71.3 | 7 | 125 | 70.4 |
| 7 | 7 | 117 | 72.4 | 5 | 126 | 68.5 |
| 8 | 6 | 116 | 76.7 | 7 | 125 | 70.1 |
| 9 | 7 | 116 | 77.0 | 6 | 118 | 69.0 |
| 10 | 6 | 115 | 74.9 | 7 | 121 | 68.7 |
| 11 | 6 | 125 | 73.7 | 7 | 123 | 67.8 |
| 12 | 6 | 137 | 71.0 | 6 | 126 | 66.3 |
| 13 | 7 | 140 | 71.7 | 6 | 123 | 65.6 |
| 14 | 6 | 139 | 72.2 | 5 | 118 | 66.4 |
| 15 | 7 | 139 | 68.1 | 7 | 120 | 67.2 |
| 16 | 6 | 138 | 68.6 | 4 | 117 | 68.5 |
| 17 | 7 | 135 | 69.0 | 7 | 114 | 70.3 |
| 18 | 7 | 132 | 68.7 | 6 | 113 | 72.3 |
| Mean Change | 6.6 | 126.2 | 73.7 + 7.9% | 6.2 | 123.1 | 68.3 |
| Mean (wk. 1–10) Change | 6.6 | 118.7 | 76.3 + 11.4% | 6.4 | 126.1 | 68.5 |
| Mean (wk. 11–18) Change | 6.5 | 135.6 | 70.4 + 3.4% | 6.0 | 119.3 | 68.1 |
| GROUP D | | | | | | |
| 1 | 6 | 144 | 70.7 | 7 | 109 | 64.9 |
| 2 | 7 | 140 | 72.5 | 6 | 112 | 64.7 |
| 3 | 6 | 137 | 72.7 | 7 | 114 | 65.1 |
| 4 | 7 | 135 | 74.9 | 6 | 121 | 65.1 |
| 5 | 6 | 133 | 76.5 | 7 | 121 | 66.9 |
| 6 | 7 | 132 | 76.2 | 7 | 126 | 64.0 |
| 7 | 5 | 132 | 74.5 | 7 | 128 | 65.6 |
| 8 | 7 | 131 | 75.1 | 6 | 129 | 69.1 |
| 9 | 6 | 129 | 74.0 | 7 | 128 | 69.8 |
| 10 | 7 | 128 | 73.2 | 6 | 132 | 70.4 |
| 11 | 7 | 127 | 72.2 | 6 | 138 | 70.8 |
| 12 | 6 | 126 | 71.3 | 6 | 137 | 70.6 |
| 13 | 6 | 125 | 71.6 | 7 | 138 | 70.3 |
| 14 | 5 | 124 | 70.4 | 6 | 138 | 71.1 |
| 15 | 7 | 128 | 70.6 | 7 | 141 | 69.9 |
| 16 | 4 | 128 | 71.1 | 6 | 140 | 70.6 |
| 17 | 7 | 132 | 68.4 | 7 | 142 | 71.3 |
| 18 | 6 | 132 | 67.7 | 7 | 143 | 71.5 |
| Mean Change | 6.2 | 130.9 | 72.4 + 5.8% | 6.6 | 129.8 | 68.4 |
| Mean (wk. 1–10) Change | 6.4 | 134.1 | 74.0 + 11.1% | 6.6 | 122.0 | 66.6 |
| Mean (wk. 11–18) Change | 6.0 | 126.9 | 70.4 − 0.6% | 6.5 | 139.6 | 70.8 |

EXAMPLE 2

A growing barn supplemented the diet of 135 calves with 1/10 th ounce per calf daily of VP-127, the product of the invention containing premium quality dried colostral powder, for a total of 138 consecutive days. An equal number of calves were fed the same diet without VP-127. This is what they reported.

|  | Fed VP-127 | Not Fed VP-127 |
| --- | --- | --- |
| Weight In (Lbs.) | 83.00 | 83.00 |
| Weight Out - Live | 417.79 | 402.44 |
| Dressed Weight | 280.84 | 270.36 |

That meant an average increase of 15.35 pounds in live weight and 10.48 in dressed weight for the calves fed VP-127. A total of 118 animals were dressed-out in the supplemented group and represented more than 1,235 extra pounds. And they found that the calves were healthier and required less medication, further reducing costs and increasing profits.

EXAMPLE 3

Efficacy Studies of Calves Treated Subcutaneously With Sterile Purified Colostrum (ID-1) at 3–6 Days of Age Calves Twenty bull calves were used in this example. The calves were fed milk replacement for nutritional support and received no supplemental colostrum. Blood samples were collected and were used to determine starting serum immunoglobulin concentration by radial immunodiffusion assay (RID).

Calves defined as having FPT were those with a serum immunoglobulin (IgG) concentration of less than 800 mg/dl and those with partial FPT with serum immunoglobulin (IgG) concentrations of 800 to 1600 mg/dL, with over 1600 mg/dL as normal (adapted from McGuire, T. C. and D. S. Adams, 1982). Because the herd had fewer calves than anticipated, some calves that were selected for the study had higher serum IgG concentration than a defined FPT level. Calves were assigned to control and treatment groups randomly and weight was determined using a dairy cattle and calf weight measuring tape.

Treatment

Calves assigned to the treatment group were injected subcutaneously with 400 ml of the product of the invention in liquid injectable form (trade name ID-1). The ID-1 contained 6.0% protein, 72% of which was immunoglobulin (IgG) (as determined by agarose gel electrophoresis). This is equivalent to 4.32 g of immunoglobulin per 100 ml of ID-1. Thus, a 100 pound calf would receive the following:

400 ml ID-1=17.28 g immunoglobulin (4×4.32 g/100 ml)

30 ml plasma/pound×100 pounds=3000 ml plasma 17.28 g/3000 ml=5.8 g of immunoglobulin (if 100% absorbed)

Sample Collection

Blood samples were collected prior to, and 24 and 48 hours after ID-1 treatment. Immunoglobulin (IgG) levels in these blood samples, as determined by radial immunodiffusion (RID), were used to demonstrate the efficacy of ID-1 in increasing serum immunoglobulin levels in calves older than 24 hours of age.

Determination of Blood Immunoglobulin Levels

Blood immunoglobulin (IgG) concentrations were determined by radial immunodiffusion (RID), with antisera specific for bovine IgG. The precipitin rings formed in the sample wells were compared to those for bovine IgG standards supplied by the manufacturer of the kit (VMRD, Pullman, WA). The ring diameters for sample and standards were entered into a computer program that then calculated the predicted concentration of immunoglobulins (IgG) in the serum.

Calculation of Percent of IgG Absorbed

The percent of IgG absorbed was calculated by comparison of the RID data from pre- and post-treatment samples. Knowing the dose of immunoglobulin given, the maximum amount of immunoglobulin that could have been absorbed, if there was 100% absorption, was calculated. From this value, and knowing the amount of IgG given, the actual percent absorption was calculated.

Results

All calves were observed to be typical "Grade B" calves. They were strong and ate the first feeding well. The next morning, all calves were sick and required much supportive therapy; all calves were treated with antibiotics, protein, and typical veal calf supportive therapy. Four of the calves in the control group died by the second day. The ID-1 treated calves seemed to respond well to the treatment, and no treated calves died. The serum immunoglobulin concentrations at 0, 24, and 48 hours are presented in Table 5.

The mean relative change at 48 hours was:

control (FPT; shaded; N=1) −31%; control (non-FPT; N=5) −16.6% treated (FPT; shaded; N=7) 57.9%; treated (non-FPT; N=3) 1%

The amount of immunoglobulin absorbed (as determined by RID, and as a calculated percentage is presented in Table 6.

The mean relative percent absorbed (calculated) was:

control (FPT; shaded; N=1) −31.2%; control (non-FPT; n=5 −23.3% treated (FPT; shaded; N=7) 79.3%; treated (non-FPT; n=3) 6.6%

From Table 6, column heading "IgG absorbed (mg/dL)", the mean absolute change in immunoglobulin concentration at 48 hours may be discerned:

control (FPT; shaded; N=1−451p control (non-FPT; N=5) 9413 treated (FPT; shaded; N=7) 334.7; treated (non-FPT; N=3) 2.3

TABLE 5

Serum immunoglobulin concentration before and after ID-1 treatment of calves 3–6 days of age. Control and treatment calves are listed in order of the pre-treatment immunoglobulin concentration.*

Serum Immunoglobulin Concentration (mg/dL)

| Calf number | Group | Pre-treatment | Post treatment (24 hrs) | Post treatment (48 hrs) | Relative treatment (24 hrs) | Relative change (48 hrs) |
|---|---|---|---|---|---|---|
| 21 | C | 1446 | 970 | 995 | −33% | −31% |
| 3 | C | 1743 | 947 | 1778 | −46% | 2% |
| 9 | C | 1992 | no sample | 1490 | no sample | −25% |
| 18 | C | 2123 | 1879 | 1594 | −11% | −25% |
| 24 | C | 3059 | 584 | 1857 | −81% | −39% |
| 27 | C | 3800 | 1378 | 3933 | −64% | 4% |
| 5 | T | 254 | 264 | 295 | 4% | 16% |
| 16 | T | 317 | 355 | 995 | 12% | 214% |
| 7 | T | 491 | 525 | 663 | 7% | 35% |
| 8 | T | 954 | 622 | 1778 | −35% | 86% |
| 10 | T | 1029 | 843 | 1328 | −18% | 29% |
| 4 | T | 1226 | 1330 | 1473 | 8% | 20% |
| 2 | T | 1538 | 1046 | 1620 | −32% | 5% |
| 29 | T | 1793 | 3011 | 1957 | 68% | 9% |
| 28 | T | 2282 | 1948 | 2219 | −15% | −3% |
| 19 | T | 3313 | 2697 | 3219 | −19% | −3% |

*Note: Data that is shaded from calves whose pre-treatment serum immunoglobulin concentrations fit the definition of complete or partial failure of passive transfer,

TABLE 6

Calculated percent immunoglobulin absorbed 48 hours after ID-1 treatment of calves 3–6 days of age. Note: Data that is shaded is from calves whose pre-treatment serum immunoglobulin concentrations fit the definition of complete or partial failure of passive transfer.

| Calf number (T/C)* | Body Weight (by tape) | Estimated ml of plasma | IgG absorbed (mg/dL)** | % absorbed (calculated) | IgG absorbed of 100% absorbed |
|---|---|---|---|---|---|
| 2(T) | 96 | 2880 | 82 | 2.1 | 395 |
| 4(T) | 96 | 2880 | 247 | 6.3 | 395 |
| 5(T) | 85 | 2550 | 41 | 9.2 | 447 |
| 7(T) | 89 | 2670 | 172 | 40.3 | 427 |
| 8(T) | 89 | 2670 | 824 | 192.9 | 427 |
| 10(T) | 89 | 2670 | 299 | 70 | 427 |
| 16(T) | 89 | 2670 | 678 | 158.8 | 427 |
| 19(T) | 96 | 2880 | −94 | −2.8 | 395 |
| 28(T) | 86 | 2580 | −63 | −14.3 | 442 |
| 29(T) | 86 | 2580 | 164 | 37 | 442 |
| 3(C) | 96 | 2880 | 35+ | 2+ | —++ |
| 9(C) | 89 | 2670 | −502 | −25.2 | — |
| 18(C) | 89 | 2670 | −529 | −25 | — |
| 21(C) | 103 | 3090 | −451 | −31.2 | — |
| 24(C) | 87 | 2610 | −1238 | −40.5 | — |
| 27(C) | 100 | 3000 | 133 | 3.5 | — |

*T = treated with 400 ml of ID-1; C untreated control calf
**calculated from RID data, Table 2; (48 hr−0 hr)
+value listed for control calves indicates change from Time 0 value, as measured at 48 hours; because they were not treated with ID-1, a percent absorption cannot be calculated
++calculation of IgG absorbed if 100% was absorbed was not performed for control calves because they were not treated with ID-1

EXAMPLE 4

Calves Treated Subcutaneously at 7 to 21 Days of Age

Calves

Twelve bull calves were used in this example. The calves were fed milk replacement for nutritional support, received no supplemental colostrum, and initial blood samples were collected and used to determine starting serum IgG concentrations (by radial immunodiffusion assay). All calves in this example had serum IgG concentrations defined as at least partial FPT. The calves were weighed, treated with the same amount of ID-1 as in Example 3, blood samples were collected in the same way as for Example 3, and determination of blood immunoglobulin levels and calculations of percent of IgG absorbed were identically performed.

Results

All calves were observed to be typical "Grade B and C" calves. They required much medication and supportive therapy; all calves were treated heavily with antibiotics. The ID-1 treated calves seemed to respond well to treatment, and no treated calves died. One control calf died. The serum immunoglobulin (IgG) concentration at 0, 24, and 48 hours is presented in Table 7. The mean relative change at 48 hours was: control (N=5) −17.4%; treated (N=7) 97.9% or (N=6) 35.7%*. The amount of immunoglobulin (IgG) absorbed (as determined by RID, and as a calculated percentage) are presented in Table 8. The mean relative percent absorbed (calculated) was: control (N=5) −22.56%; treated (N=7) 111.6% or (N=6) 71.1%*. From Table 8, column heading "IgG absorbed (mg/dL)", the mean absolute range of immunoglobulin concentration at 48 hours may be discerned: control (N=5) −154%; treated (N=7) 518.4% or (N=6) 282.8%*. (if number 207 is not included in calculation; its change at 48 hours was 471%).

TABLE 7

Serum immunoglobulin concentration before and after ID-1 treatment of calves 7–21 days of age. Control and treatment calves are listed in order of the pre-treatment immunoglobulin concentration.

Serum Immunoglobulin Concentration (mg/dL)

| Calf number | Group | Pre-treatment | Post treatment (24 hrs) | Post treatment (48 hrs) | Relative treatment (24 hrs) | Relative change (48 hrs) |
|---|---|---|---|---|---|---|
| 175 | C | 321 | 276 | 364 | −14% | 13% |
| 185 | C | 354 | 396 | 177 | 12% | −50% |
| 208 | C | 432 | 423 | 408 | −2% | −6% |
| 215 | C | 1151 | 1436 | 728 | 25% | −37% |
| 206 | C | 1431 | 2039 | 1329 | 42% | −7% |
| 204 | T | 233 | 356 | 341 | 53% | 46% |
| 207 | T | 410 | 1399 | 2342 | 241% | 471% |
| 188 | T | 542 | 507 | 646 | −6% | 19% |
| 192 | T | 866 | 982 | 1261 | 13% | 46% |
| 198 | T | 1024 | 1563 | 1471 | 53% | 44% |
| 214 | T | 1091 | 1634 | 1699 | 50% | 56% |
| 210 | T | 1215 | 1531 | 1250 | 26% | 3% |

TABLE 8

Calculated percent immunoglobulin absorbed 48 hours
after ID-1 treatment of calves 7–21 days of age.

| Calf number (T/C)* | Body Weight (by tape) | Estimated ml of plasma | IgG absorbed (mg/dL)** | % absorbed (calculated) | IgG absorbed of 100% absorbed |
|---|---|---|---|---|---|
| 188(T) | 96  | 2880 | 104   | 22    | 476 |
| 192(T) | 103 | 3090 | 395   | 81    | 443 |
| 198(T) | 103 | 3090 | 447   | 99    | 443 |
| 204(T) | 94  | 2820 | 108   | 22    | 489 |
| 207(T) | 84  | 2520 | 1932  | 355   | 544 |
| 210(T) | 110 | 3300 | 35    | 8.4   | 415 |
| 214(T) | 146 | 4380 | 608   | 194   | 313 |
| 185(T) | 114 | 3420 | −177+ | −50+  | —++ |
| 206(T) | 84  | 2520 | −104  | −7    | — |
| 208(T) | 89  | 2670 | −24   | −5.6  | — |
| 175(C) | 85  | 2550 | −42   | −13.4 | — |
| 215(C) | 122 | 3660 | −423  | −36.8 | — |

*= treated with 400 ml of ID-1; C untreated control calf
**calculated from RID data, Table 7; (48 hr–0 hr)
+value listed for control calves indicates change from Time 0 value, as measured at 48 hours; because they were not treated with ID-1, a percent absorption cannot be calculated
++calculation of IgG absorbed if 100% was absorbed was not performed for control calves because they were not treated with ID-1

EXAMPLE 5

Calves Treated Subcutaneously or Intravenously at 3–7 Days of Age

Calves

Thirty-nine bull calves were used in this example. The calves were fed milk replacement for nutritional support. The calves did not receive any supplemental colostrum. Blood samples were collected from calves and were used to determine the baseline serum IgG concentration (by radial immunodiffusion assay; RID). Because the baseline IgG concentration cannot be predicted before it is actually measured, some calves had higher serum IgG concentrations than the defined FPT level. Calves were assigned to control and treatment groups randomly, at the time of the first bleeding. Weight was determined using a Dairy Cattle and Calf Weight Measuring Tape. The 12 calves assigned to the control group were untreated.

Subcutaneous Treatment

The 19 calves assigned to the subcutaneous treatment group were injected with 400 ml of ID-1. The ID-1 contained 6.0% protein, 72% of which was immunoglobulin (IgG) as determined by agarose gel electrophoresis. This is equivalent to 4.32 g of immunoglobulin (IgG) per 100 ml of ID-1.

Intravenous Treatment

The eight (8) calves assigned to the intravenous treatment group were injected with 240 ml of ID-1. The ID-1 contained the same amount of protein and immunoglobulin as described above, and is equivalent to 4.32 g of immunoglobulin (IgG) per 100 ml of ID-1.

Sample Collection

Blood samples were collected prior to, and 24 and 48 hours after ID-1 treatment. Immunoglobulin (IgG) levels in these blood samples, as determined by RID, were used to demonstrate the efficacy of ID-1 in increasing serum immunoglobulin (IgG) levels in calves 3–7 days of age as described earlier.

RESULTS

All calves were observed to be typical "Grade B" calves. Many calves appeared sickly and had what appeared to be nutritional diarrhea, but supportive therapy was delayed until after the 48-hour blood sample was collected. Two of the calves, one in the control group and one in the IV treatment group died before the 24 hour blood sample could be taken.

The serum immunoglobulin (IgG) concentrations at 0, 24, and 48 hours are presented in Tables 9 and 10. The mean relative change at 24 and 48 hours was:

Mean relative change at 24 hours:

control (FPT; shaded; N=5) 42.8%; control (non-FPT; N=6) −4.3%

IV treated (FPT; shaded; N=4) 95.8%; IV treated (non-FPT; N=3) 25.3%

SQ treated (FPT; shaded; N=8) 85.5%; SQ treated (non-FPT; N=11) 23.9%

Mean relative change at 48 hours:

control (FPT; shaded; N=5) 32.8%; control (non-FPT; N=6) −8.8%

IV treated (FPT; shaded; N=4) 84.3%; IV treated (non-FPT; N=3) 45.3%

SQ treated (FPT; shaded; N=8) 116.1%; SQ treated (non-FPT; N=11) 7.4%

The amount of immunoglobulin (IgG) absorbed (as determined by RID, and as calculated percentage) are presented in Tables 11 and 12. The mean relative percent absorbed (calculated) was:

Mean relative % absorbed at 24 hours:

control (FPT; shaded; N=5) 14.0%; control (non-FPT; N=6) −6.3%

IV treated (FPT; shaded; N=4) 83.5%; IV treated (non-FPT; N=3) 216.7%

SQ treated (FPT; shaded; N=8) 50.1%; SQ treated (non-FPT; N=11) 166.8%

Mean relative % absorbed at 48 hours:

control (FPT; shaded; N=5) 13.6%; control (non-FPT; N=6) −7.0%

IV treated (FPT; shaded; N=4) 77.5%; IV treated (non-FPT; N=3) 473.7%

SQ treated (FPT; shaded; N=8) 92.6%; SQ treated (non-FPT; N=11) 36.4%

From Tables 11 and 12, column headings "IgG observed (mg/dL)" and "IgG absorbed (mg/dL)", the mean absolute change in immunoglobulin concentration at 24 and 48 hours may be discerned:

Mean absolute change at 24 hours:

control (FPT; shaded; N=5) 35.0%; control (non-FPT; N=6) −19.3%

IV treated (FPT; shaded; N=4) 214.5%; IV treated (non-FPT; N=3) 512.7%

SQ treated (FPT; shaded; N=8) 209.8%; SQ treated (non-FPT; N=11) 687.2%

Mean absolute change at 24 hours:

control (FPT; shaded; N=5) −23.6%; control (non-FPT; N=6) 295.7%

IV treated (FPT; shaded; N=4) 195.5%; IV treated (non-FPT; N=3) 1145.7%

SQ treated (FPT; shaded; N=8) 370.8%; SQ treated (non-FPT; N=11) 156.1%

TABLE 9

Serum immunoglobulin concentration before and after ID-1 treatment of calves 7–21 days of age. Control and VI treatment calves are listed in order of the pre-treatment immunoglobulin concentration.

Serum Immunoglobulin Concentration (mg/dL)

| Calf number | Group | Pre-treatment | Post treatment (24 hrs) | Post treatment (48 hrs) | Relative treatment (24 hrs) | Relative change (48 hrs) |
|---|---|---|---|---|---|---|
| 1486 | C | 37 | 114 | 87 | 208% | 135% |
| 1465 | C | 181 | 168 | 211 | -7% | 17% |
| 1458 | C | 268 | 298 | 390 | 11% | 46% |
| 1469 | C | 704 | 647 | 556 | -8% | -21% |
| 1574 | C | 1327 | 1465 | 1155 | 10% | -13% |
| 1480 | C | 2412 | 2236 | 1894 | -7% | -21% |
| 1491 | C | 2571 | 1879 | 1193 | -27% | -54% |
| 1483 | C | 3310 | 3149 | 9260 | -5% | 180% |
| 1577 | C | 3314 | 3244 | 2981 | -2% | -10% |
| 1569 | C | 4629 | 4826 | 2622 | 4% | -43% |
| 1475 | C | 7213 | 7999 | 7273 | 11% | 1% |
| 1468 | IV | 116 | 238 | 125 | 105% | 8% |
| 1575 | IV | 163 | 315 | 423 | 93% | 160% |
| 1457 | IV | 254 | 476 | 476 | 87% | 87% |
| 1655 | IV | 354 | 716 | 645 | 102% | 82% |
| 1559 | IV | 1696 | 2348 | 2303 | 38% | 36% |
| 1653 | IV | 2371 | 3300 | 4280 | 39% | 81% |
| 1489 | IV | 4799 | 4756 | 5720 | -1% | 19% |

Note: Data that is shaded is from calves whose pre-treatment serum immunoglobulin concentrations fit the definition of complete or partial failure of passive transfer.

TABLE 10

Serum immunoglobulin concentration before and after ID-1 treatment of calves 3–7 days of age. Subcutaneous treatment calves are listed in order of the pre-treatment Immunoglobulin concentration.*

Serum Immunoglobulin Concentration (mg/dL)

| Calf number | Group | Pre-treatment | Post treatment (24 hrs) | Post treatment (48 hrs) | Relative treatment (24 hrs) | Relative change (48 hrs) |
|---|---|---|---|---|---|---|
| 1485 | SQ | 87 | 298 | 244 | 243% | 180% |
| 1461 | SQ | 98 | 208 | 231 | 112% | 136% |
| 1459 | SQ | 163 | 298 | 613 | 83% | 276% |
| 1566 | SQ | 209 | 526 | 591 | 152% | 183% |
| 1481 | SQ | 510 | 715 | 678 | 40% | 33% |
| 1487 | SQ | 1172 | 1384 | 1193 | 18% | 2% |
| 1479 | SQ | 1340 | 1733 | 1644 | 29% | 23% |
| 1463 | SQ | 1408 | 1503 | 2759 | 7% | 96% |
| 1576 | SQ | 1756 | 3065 | 2048 | 75% | 17% |
| 1466 | SQ | 1826 | 2182 | 2170 | 19% | 19% |
| 1573 | SQ | 2584 | 3846 | 3400 | 49% | 32% |
| 1565 | SQ | 2909 | 3865 | 2934 | -2% | 1% |
| 1472 | SQ | 2910 | 3664 | 3145 | 26% | 8% |
| 1490 | SQ | 3109 | 2946 | 3442 | -5% | 11% |
| 1570 | SQ | 3468 | 3634 | 3400 | 5% | -2% |
| 1482 | SQ | 3524 | 2939 | 4135 | -17% | 17% |
| 1484 | SQ | 3750 | 4433 | 3786 | 18% | 1% |
| 1578 | SQ | 3953 | 3765 | 2463 | -5% | -38% |
| 1478 | SQ | 3990 | 7999 | 4573 | 100% | 15% |

Note: Data that is shaded is from calves whose pre-treatment serum immunoglobulin concentrations fit the definition of complete or partial failure of passive transfer.

TABLE 11

Calculated percent immunoglobulin (IgG) present in blood 24 and 48 hours after ID-1 treatment of calves 3–7 days of age. Data for control and IV treatment calves is listed in order of ear tag number. Note: Data that is shaded is from calves whose pre-treatment serum immunoglobulin concentrations fit the definition of complete or partial failure of passive transfer.

| Calf number/ group* | Body weight | Estimated ml of plasma | IgG available if 100% present | IgG observed (mg/dl) (24 hrs)** | % present (calculated) (24 hrs) | IgG observed (mg/dl) (48 hrs)** | % present (calculated) (48 hrs) |
|---|---|---|---|---|---|---|---|
| 1458/C | 85 | 2550 | — | 30 | 10% | 122 | 41% |
| 1465/C | 89 | 2670 | — | -13 | -8% | 30 | 18% |
| 1469/C | 82 | 2460 | — | -57 | -9% | -148 | -23% |
| 1475/C | 89 | 2670 | — | 786 | 10% | 60 | 1% |
| 1480/C | 94 | 2820 | — | -176 | -8% | -518 | -23% |
| 1483/C | 85 | 2550 | — | -161 | -5% | 5950 | 189% |
| 1486/C | 103 | 3090 | — | 77 | 68% | 50 | 44% |
| 1491/C | 85 | 1550 | — | -692 | -37 | -1378 | -73% |
| 1569/C | 89 | 2670 | — | 197 | 4% | -2007 | -42% |
| 1574/C | 89 | 2670 | — | 138 | 9% | -172 | -12% |
| 1577/C | 94 | 2820 | — | -70 | -2% | -333 | -10% |
| 1457/IV | 82 | 2460 | 278 | 222 | 80% | 222 | 80% |
| 1468/IV | 89 | 2670 | 256 | 122 | 48% | 9 | 4% |
| 1489/IV | 82 | 2460 | 278 | -43 | -15% | 921 | 331% |
| 1559/IV | 86 | 2570 | 266 | 652 | 245% | 607 | 228% |
| 1575/IV | 98 | 2940 | 233 | 152 | 65% | 260 | 112% |
| 1653/IV | 103 | 3090 | 221 | 929 | 420% | 1909 | 862% |
| 1655/IV | 89 | 2670 | 256 | 362 | 141% | 291 | 114% |

*IV = treated intravenously with 240 ml of ID-1; C = untreated control calf
**calculated from RID data, Table 9; (24 hr–0 hr; 48 hr–0 hr)

TABLE 12

Calculated percent immunoglobulin (IgG) absorbed in blood 24 and 48 hours after ID-1 treatment of calves 3–7 days of age. Data for SQ treatment calves is listed in order of ear tag number. Note: Data that is shaded is from calves whose pre-treatment serum immunoglobulin concentrations fit the definition of complete or partial failure of passive transfer.

| Calf number/ group* | Body weight | Estimated ml of plasma | IgG absorbed if 100% absorbed | IgG absorbed (mg/dL) (24 hrs)** | % absorbed (calculated (24 hrs) | IgG absorbed (mg/dL) (48 hrs)** | % absorbed (calculated) (48 hrs) |
|---|---|---|---|---|---|---|---|
| 1459/SQ | 82 | 2460 | 463 | 135 | 29% | 450 | 97% |
| 1461/SQ | 89 | 2670 | 427 | 110 | 26% | 133 | 31% |
| 1463/SQ | 103 | 3090 | 369 | 95 | 26% | 1351 | 366% |
| 1466/SQ | 89 | 2670 | 427 | 356 | 83% | 344 | 81% |
| 1472/SQ | 84 | 2520 | 452 | 754 | 167% | 235 | 52% |
| 1478/SQ | 87 | 2610 | 437 | 4009 | 918% | 583 | 133% |
| 1479/SQ | 91 | 2730 | 418 | 393 | 94% | 304 | 73% |
| 1481/SQ | 85 | 2550 | 447 | 205 | 46 | 168 | 38% |
| 1482/SQ | 83 | 2490 | 458 | −585 | −128% | 611 | 133% |
| 1484/SQ | 94 | 2820 | 404 | 683 | 169% | 36 | 9% |
| 1485/SQ | 82 | 2460 | 463 | 211 | 46% | 157 | 34% |
| 1487/SQ | 96 | 2880 | 396 | 212 | 54% | 21 | 5% |
| 1490/SQ | 89 | 2670 | 427 | −163 | −38% | 333 | 78% |
| 1565/SQ | 96 | 2880 | 396 | −44 | −11% | 25 | 6% |
| 1566/SQ | 96 | 2880 | 396 | 317 | 80% | 382 | 97% |
| 1570/SQ | 96 | 2880 | 396 | 166 | 42% | −68 | −17% |
| 1573/SQ | 100 | 3000 | 380 | 1262 | 322% | 816 | 215% |
| 1576/SQ | 89 | 2670 | 427 | 1309 | 307% | 292 | 68% |
| 1578/SQ | 91 | 2730 | 418 | −188 | −45% | −1490 | −357% |

*SQ = treated intravenously with 400 ml of ID-1; C = untreated control calf
**calculated from RID data, Table 9; (24 hr–0 hr; 48 hr–0 hr)

What is claimed is:

1. A protein rich whey product derived from colostrum comprising:
a preparation of bovine colostrum from which fat and casein have been removed; said preparation comprising immunoglobulins and nonspecific proteins selected from the group consisting of transferin, lactoferin, lysozyme, xanthine oxidase, lactoperoxidase, insulin-like growth promoting factors, conglutinin, β-lysin and ubiquitin including those with a size of less than 10,000 Daltons.

2. A method of treatment for failure of passive immunity transfer (FPT) in calves, said method comprising:
collecting colostrum from dairy cows;
removing casein and fat from said colostrum to produce a protein-rich when product comprising immunoglobulins and nonspecific proteins including proteins having a size of less than 10,000 Daltons present in said colostrum;
sterilizing said preparation; and administering said preparation to a calf following gut closure.

3. The method of claim 2 wherein said nonspecific proteins in part increase cellular immunity and stimulate cellular activity.

4. The method of claim 2 wherein said preparation is injected into a calf.

5. The method of claim 2 wherein said blood immunoglobulin and nonspecific protein concentration is increased in calves over 24 hours old.

6. The method of claim 2 wherein said preparation results in blood immunoglobulin levels of at least one-fourth that of a normal calf that has received passive immunity within 24 hours after administration.

7. The method of claim 2 wherein 70% to 80% of subcutaneously injected immunoglobulin is absorbed.

8. A method of treatment for failure of passive immunity transfer in calves, said method comprising:
collecting bovine colostrum;
removing casein and fat from said collected colostrum, to prepare a protein-rich whey product from remaining immunoglobulins and nonspecific proteins present in said colostrum;
sterilizing said protein-rich whey product for injection, and
injecting an effective amount of said protein-rich whey product into an affected calf, said calf being at an age where its gut has essentially closed.

9. The method of claim 8 wherein 100% of immunoglobulin administered is immediately utilized by the affected calves.

10. The method of claim 8 wherein the affected calves exhibits no swelling or discomfort from injection.

11. The method of claim 8 wherein said bovine colostrum contains immunoglobulins and nonspecific proteins.

12. The method of claim 11 wherein said nonspecific proteins impart increased cellular immunity to affected calves.

13. The method of claim 8 wherein said calf is from 24 hours to 21 days old.

14. The method of claim 8 wherein said serum is a colostrum replacement.

15. A method of preparing a product for improving milk production in cows comprising:
collecting colostrum from dairy cows;
removing casein and fat from said colostrum to produce a purified protein-rich whey product comprising of immunoglobulins and nonspecific proteins selected from the group consisting of transferin, lactoferin, lysozyme, xanthine oxidase, lactoperoxidase, insulin-like growth promoting factors, conglutinin, β-lysin and ubiquitin present in said colostrum, wherein said proteins include those with a size of less than 10,000;

sterilizing said preparation; and administering said preparation to a cow following gut closure.

16. The method of claim 15 further comprising the step of drying said preparation to form a powder.

17. A method of improving milk production in adult and young cows comprising:

supplementing the diet of said cows with a dried purified protein-rich whey product derived from bovine colostrum, wherein the product includes proteins having a size of less than 10,000 Daltons, and further providing that said product is used to supplement the diet of said cows following gut closure.

18. The method of claim 1 wherein said supplementation is 1/10–2/5 oz. of product per cow per day.

* * * * *